United States Patent [19]

Zacca et al.

[11] Patent Number: 5,308,354
[45] Date of Patent: May 3, 1994

[54] ATHERECTOMY AND ANGIOPLASTY METHOD AND APPARATUS

[76] Inventors: Nadim M. Zacca, 6550 Fannin St., Ste. 2229, Houston, Tex. 77030; Martin R. Jasso, 11655 Sagelink Dr., Houston, Tex. 77089

[21] Appl. No.: 805,577

[22] Filed: Dec. 10, 1991

Related U.S. Application Data

[63] Continuation-in-part of Ser. No. 731,109, Jul. 15, 1991, Pat. No. 5,217,474.

[51] Int. Cl.⁵ .............................................. A61B 17/32
[52] U.S. Cl. .................................... 606/159; 606/170; 606/180; 606/194
[58] Field of Search ............... 606/159, 170, 171, 180, 606/194, 198; 604/22, 104–109

[56] References Cited

U.S. PATENT DOCUMENTS

| | | | |
|---|---|---|---|
| 2,541,691 | 2/1951 | Eicher | 27/24 |
| 2,730,101 | 1/1956 | Hoffman | 128/305 |
| 2,816,552 | 12/1957 | Hoffman | 128/305 |
| 3,283,353 | 11/1966 | Kirk | 15/104.3 |
| 3,320,957 | 5/1967 | Sokolik | 606/170 |
| 3,749,085 | 7/1973 | Willson et al. | 128/2 B |
| 4,030,503 | 6/1977 | Clark, III | 128/304 |
| 4,273,128 | 6/1981 | Lary | 606/159 |
| 4,445,509 | 5/1984 | Auth | 128/305 |
| 4,646,736 | 3/1987 | Auth | 128/303 R |
| 4,653,496 | 3/1987 | Bundy et al. | 128/305 |
| 4,655,217 | 4/1987 | Reed | 128/305 |
| 4,706,671 | 11/1987 | Weinrib | 128/348.1 |
| 4,762,130 | 8/1988 | Fogarty et al. | 128/348.1 |
| 4,765,332 | 8/1988 | Fischell et al. | 128/305 |
| 4,772,258 | 9/1988 | Marangoni et al. | 604/22 |
| 4,794,928 | 1/1989 | Kletschka | 128/344 |
| 4,834,093 | 5/1989 | Littleford et al. | 128/303 |
| 4,842,579 | 6/1979 | Shiber | 604/22 |
| 4,848,342 | 7/1989 | Kaltenbach | 604/104 |
| 4,885,003 | 12/1989 | Hillstead | 604/22 |
| 4,890,611 | 1/1990 | Monfort et al. | 606/159 |
| 4,892,519 | 1/1990 | Songer et al. | 606/194 |
| 4,895,560 | 1/1990 | Papantonakos | 604/22 |
| 4,909,781 | 3/1990 | Husted | 604/22 |
| 4,966,604 | 10/1990 | Reiss | 606/159 |
| 4,979,951 | 12/1990 | Simpson | 606/159 |

(List continued on next page.)

FOREIGN PATENT DOCUMENTS 0268228 5/1988 European Pat. Off.
0421457A1 5/1990 European Pat. Off.

*Primary Examiner*—Edgar S. Burr
*Assistant Examiner*—Ren Yan
*Attorney, Agent, or Firm*—William E. Shull

[57] ABSTRACT

A device for treating obstructions in vessels or small openings in the body, comprising a rotatable ablator tip which is guided to the obstruction in a reduced diameter configuration, expanded and rotated to remove the obstruction, and contracted to remove the device from the body. The variably expandable abrasive tip coil in one embodiment is actuated by piston means within the coil. A pair of collars is attached to the ends of the coil, and the piston effects relative longitudinal axial movement of the collars and the respective ends of the coil tip. When the ends of the coil tip are so moved, expansion and contraction of the diameter of the coil tip results. In another embodiment, the expansion tip coil is actuated by an expandable and contractible bellows disposed within the coil. In another embodiment, the expansion and contraction of the coil tip are effected by longitudinal axial movement of an internal coil attached to one end of the coil tip, within an outer coil attached to its other end. In another embodiment, expansion and contraction of the coil tip are effected by an inflatable balloon disposed within the coil tip. The balloon expansion means enlarges preferably at the central portion of the coil to make a bulge. In alternative embodiments, there is provided a combined atherectomy and balloon angioplasty device employing either a fixed or variable diameter rotatable abrasive burr, and an angioplasty balloon disposed proximal to the burr.

11 Claims, 11 Drawing Sheets

U.S. PATENT DOCUMENTS

| | | | |
|---|---|---|---|
| 4,986,807 | 1/1991 | Farr | 604/22 |
| 4,990,134 | 2/1991 | Auth | 604/22 |
| 4,994,067 | 2/1991 | Summers | 606/159 |
| 5,007,896 | 4/1991 | Shiber | 604/22 |
| 5,009,659 | 4/1991 | Hamlin et al. | 606/159 |
| 5,019,088 | 5/1991 | Farr et al. | 606/159 |
| 5,019,089 | 5/1991 | Farr | 606/172 |
| 5,024,651 | 6/1991 | Shiber | 604/22 |
| 5,026,384 | 6/1991 | Farr et al. | 606/159 |
| 5,030,201 | 7/1991 | Palestrant | 604/22 |
| 5,041,082 | 8/1991 | Shiber | 604/22 |
| 5,042,984 | 8/1991 | Kensey et al. | 606/128 |
| 5,047,040 | 9/1991 | Simpson | 606/159 |
| 5,049,154 | 9/1991 | Quadri | 606/159 |
| 5,053,044 | 10/1991 | Mueller et al. | 606/159 |
| 5,059,203 | 10/1991 | Husted | 606/159 |
| 5,071,424 | 12/1991 | Reger | 606/159 |
| 5,074,841 | 12/1991 | Ademovic et al. | 604/22 |
| 5,074,871 | 12/1991 | Groshong | 606/170 |
| 5,078,722 | 1/1992 | Stevens | 606/159 |
| 5,078,723 | 1/1992 | Dance et al. | 606/159 |
| 5,100,424 | 3/1992 | Jang et al. | 606/159 |

ATHERECTOMY AND ANGIOPLASTY METHOD AND APPARATUS

CROSS REFERENCES TO RELATED APPLICATIONS

This application is a continuation-in-part of Applicants' prior copending U.S. application Ser. No. 07/731,109, filed Jul. 15, 1991, now U.S. Pat. No. 5,217,474, and Applicants' prior copending International Applicational Serial Number PCT/US91/06381, filed Sep. 5, 1991, the disclosures of which are incorporated herein by reference, and the benefits of the filing dates of which are hereby claimed.

BACKGROUND OF THE INVENTION

1. Field of the Invention

The present invention relates in general to devices for removing obstructions from vessels or small openings in the body, and more particularly to a rotatable ablator tip which is guided to the obstruction in a reduced diameter configuration, expanded and rotated to remove the obstruction, and contracted to remove the device from the body. The present invention further relates to a combined atherectomy and balloon angioplasty device having a rotatable ablator tip of either a fixed or a variable diameter, and an angioplasty balloon disposed proximally of the ablator tip.

2. Background Art

There has been great interest of late among those in the medical community in nonsurgical means to remove obstructions from occluded vessels, particularly coronary arteries. Traditionally, patients have had to undergo relatively complex, invasive, and risky coronary bypass surgery in order to obviate or reduce the obvious health hazards presented by occluded coronary arteries. Coronary bypass surgery typically involves utilizing vascular tissue from another part of the patient's body, such as his leg, and constructing a shunt around the obstructed vessel. The obstruction can be formed of a relatively hard material, such as a plaque deposit, or a softer material such as a fibrinogen polymerized to form a thrombus.

An alternative to the traditional coronary bypass surgery which has become popular in recent years is a technique known as balloon angioplasty. In this technique, a deflated balloon is introduced by means of a catheter to the obstructed area. The balloon is then inflated to open the lumen of the vessel. The inflated balloon tends to crush or compact the obstructing material against the vessel walls as well as crack the obstructing material and dilate the vessel so as to increase the lumen or passageway therethrough, but does not remove the obstructing material from the vessel. Since the cracked and fractured obstructing material is not removed, there is a significant possibility that the vessel will become reoccluded at the treated area within a relatively short period of time, thus requiring additional treatment(s). The balloon angioplasty procedure has several additional drawbacks which tend to further reduce its desirability and/or effectiveness. In the case of a severely occluded vessel, it may be difficult to position the deflated balloon so that it spans the occlusion without causing undue trauma to the surrounding vasculature. This is because the leading portion of the balloon must first be forced through the occlusion into position for treatment. The balloon angioplasty procedure is not satisfactory for treating calcified and hard occlusions, since it may not be able to crack and dilate the obstructing material. The balloon angioplasty procedure also is not satisfactory for treating eccentric occlusions, i.e., occlusions which occur primarily on one side of the vessel, because the balloon tends to simply stretch the healthy vascular tissue and not to compress the occluding material. After the balloon is deflated, the healthy vascular tissue returns to its normal shape and the occlusion remains essentially untouched. Moreover, the balloon angioplasty technique is less suitable for treating lengthy occlusions or those occurring at curves and bends in the vessels, due to the difficulty of appropriately placing and properly inflating the balloons without the high risk of dissections. In addition, during the balloon angioplasty technique, there is a period of time during which the vessel is essentially totally obstructed by the balloon. This could lead to further damage to tissues already damaged, or even to damage to previously healthy tissues. Moreover, when the balloon inflates, it may cause uncontrolled deep injury to the vessel, including the formation of intraluminal flaps, which may in turn result in abrupt closure or predispose to a high rate of restenosis.

Atherectomy is another technique developed of late for opening the lumen of an occluded vessel, and, like the balloon angioplasty technique, provides an alternative to the traditional coronary bypass surgery. Atherectomy involves physically breaking up the material which blocks or partially blocks the vessel. Several types of atherectomy devices have been developed. U.S. Pat. Nos. 4,990,134 and 4,445,509 to Auth disclose a rotatable burr with a fluted or abrasive surface that is introduced into the obstructed vessel. At the obstruction the burr is rotated at a high rate of speed to abrade or cut away at the obstruction. The burr is a solid tip that is introduced into the vessel with a catheter and remotely driven to rotate at the desired speed. The burr is introduced into the patient's body typically at the femoral artery and guided to the obstructed vessel.

The rotatable burr atherectomy devices of the prior art when properly used have several advantages over the balloon angioplasty technique. Unlike the balloon angioplasty technique, treating an occluded vessel with a rotatable burr essentially completely removes the obstructing material, leaving the vessel wall relatively smooth and eliminating the bits or flaps of tissue at the treatment site which often result from balloon angioplasty. Moreover, unlike the balloon angioplasty device, a rotatable burr can effectively remove eccentric occlusions, because the rotating burr tends to "slide off" the healthy vascular tissue on one side of the vessel and to selectively abrade the occluding material on the other side of the vessel. Furthermore, a rotatable burr, which abrades as it progresses, can effectively treat a relatively long occlusion, and tight and/or calcified occlusions.

One major drawback with traditional rotatable burr atherectomy devices is that they have a fixed working diameter. That is, the cutting size is fixed and cannot be varied to accommodate a range of vessel openings. When it is necessary to clear a relatively large vessel which has become severely occluded, typically a physician will be reluctant to use a burr of sufficient diameter to clear the vessel all at once. This necessitates the use of two or more successively larger diameter burrs. Moreover, many times the prior art atherectomy procedure must be assisted by a balloon procedure in order to achieve an adequate result. The above tends to lengthen and complicate the procedure and make it costly. In order to get a large diameter burr to the site of the obstruction, it must first be introduced into the patient's body through an introducer sheath, typically in the patient's leg, and guided through the patient's vascular system to the obstructed vessel. Large burrs require appropriately large introducer sheaths, which ten to cause increased vascular tissue trauma at the site of introduction. Large burrs also tend to cause increased vascular tissue trauma as they are guided through the patient's vascular system to the obstruction site. Large burrs might also interfere with or disturb other occlusions along the way to the target occlusion, such other occlusions being otherwise too small to indicate treatment. For example, it has been found that it is better not to treat or disturb occlusions of less than about 50%-60%, since treatment of such lesions entails greater risks to the patient's health than leaving them untreated or undisturbed. A large diameter burr could tend to disturb such small lesions in passage, even to the extent that they become health-threatening. In addition, because prior art burrs have had an abrading surface on only their forward or distal surfaces, physicians have encountered difficulty in satisfactorily treating occlusions at curved vessel locations. Accordingly, physicians faced with the prospects of having to introduce, guide, and then manipulate in the obstructed area a relatively large burr might choose to avoid the rotatable burr technique altogether and fall back to a less desirable alternative, such as balloon angioplasty or even bypass surgery.

Thus, there is a clear need in the medical community for an atherectomy device which possesses all the advantages of the traditional rotatable burr device over the balloon angioplasty technique, but yet can be introduced into the patient's body with a relatively small introducer sheath, thus minimizing tissue trauma at the introduction site; can be guided to the obstruction site with minimal vascular tissue trauma and using smaller guiding catheters; can pass through non-targeted (smaller) occlusions with minimal contact; and can be used to treat openings of varying size during the same procedure. It will be appreciated that such a device would eliminate the need for multiple procedures with varying sized burrs, and would eliminate the reluctance of physicians to use the rotatable burr technique in the first place due to the disadvantages they see with the larger, fixed diameter burrs. There is also a need for such a device having an abrading surface on its proximal face as well as on its distal face, to facilitate treating occlusions at curved vessel sites.

Other atherectomy devices with rotatable expandable blades have been disclosed in U.S. Pat. No. 4,966,604 to Reiss and U.S. Pat. No. 4,895,560 to Papantonakos. Although the blades expand to accommodate variable vessel size, sensor devices or other means must be used during the expansion of the instrument and cutting because the blades can injure or puncture the vessel to be repaired in addition to cutting away the obstruction.

At times, there may arise situations wherein it would be advantageous or desirable to combine the benefits of an atherectomy procedure with the capabilities of a balloon angioplasty procedure to accomplish the intended or required results. For example, sometimes a dissection of vascular tissue may occur during an atherectomy procedure, creating a "flap" of tissue which may not be easily removed with the rotatable tip.

It has been found that an angioplasty balloon may be used in such cases to "tack" the flap of tissue back to the vessel wall to promote healing of the vessel at the site of the dissection. With the prior art devices presently available, such a tacking procedure can only be effected after the atherectomy device is removed from the patient's body and a balloon angioplasty catheter inserted in its place. This unduly lengthens and complicates the overall procedure. Moreover, at times physicians might be reluctant to use an atherectomy burr of a large enough diameter to fully open an occluded vessel, even when presented with the opportunity of using an expandable-type burr as disclosed herein, which as stated earlier can be introduced into the occluded vessel in a reduced diameter state. In such cases, the physician might choose to use a smaller diameter rotatable burr to perform the atherectomy procedure, and then follow with a balloon angioplasty procedure to attempt to open the vessel further, to the ultimate desired diameter. Again, with the prior art devices presently available, such a two-step procedure comprising both atherectomy and balloon angioplasty can only be effected after the atherectomy device is removed from the patient's body and a balloon angioplasty catheter inserted in its place. As noted above, this unduly lengthens and complicates the overall procedure.

SUMMARY OF THE INVENTION

The present invention comprises apparatus and methods for removing obstructions from vessels or small openings in the body. The apparatus is guided into the vessel having the obstruction. The tip of the apparatus comprises a short length of ovaloid shaped coil that can be elongated, thereby decreasing its circumference as compared to its circumference in the normal wound configuration. Lengthening and rotating the coil reduce its circumference and facilitate its introduction to an obstructed area. The coil is then allowed to return to a normal wound configuration thereby increasing the overall circumference of the coil. At least part of the outer surface of the coil is abrasive. The coil can be enlarged to a preselected circumference between the normal wound configuration and the elongated smaller circumference. The coil is rotated at the point of the obstruction to break up the obstruction and clear the vessel. The above ovaloid shaped coil resembles a spiral lemon peel.

Preferably the coil is tightly wound and multifilar, preformed in an ovoid shape. The coil typically surrounds a means for facilitating introduction into the vessel where the obstruction is located, such as a catheter with a lumen for guide wire insertion. The coil is held at one end by a tapered tip at the end of the catheter. The coil is connected to a means for rotation.

The coil diameter can be selectively decreased and increased as desired to reach and treat, respectively, the obstruction in the vessel. The coil's circumference can be increased or decreased over a range by a remotely actuated means that will elongate or retract the coil as desired. This permits the use of introducers and guiding catheters of smaller diameters than is common in the present practice of device introduction, resulting in less trauma to the patient's vessels at the site of introduction and en route to the obstruction, and also simplifying the procedure.

The present invention comprises a variably expandable abrasive tip coil which may be rotated at the point of obstruction. In one embodiment of the invention, the expansion tip coil is actuated by a piston means disposed within the coil. A pair of collars is attached to the ends of the coil, and the piston effects relative longitudinal axial movement of the collars and, hence, the respective ends of the coil tip. When the ends of the coil tip are so moved with respect to one another, expansion and contraction of the diameter of the coil tip results. In another embodiment of the invention, the expansion tip coil is actuated by an expandable and contractible bellows means disposed within the coil, instead of the piston means. In another embodiment of the invention, the expansion and contraction of the coil tip are effected by longitudinal axial movement of an internal coil attached to one end of the coil tip, within an outer coil attached to the other end of the coil tip. In another embodiment of the invention, expansion and contraction of the coil tip are effected by an inflatable balloon disposed within the coil tip. The balloon expansion means enlarges preferably at the central portion of the coil to make a bulge.

The ability of the tip to adjust to a desired diameter, within the maximum and minimum range, permits the progressive, from smaller to larger, enlargement of a passage through a stenotic obstruction. The variable tip diameter permits the use of a single device of the present invention to more fully clear a stenosis without the need to use two or more of the existing fixed diameter atherectomy devices. The present treatment of stenosis, with fixed diameter atherectomy devices, in addition to requiring the use of two or more cutting devices almost always requires the use of an angioplasty balloon catheter as a final treatment. A single device of the present invention will fully treat a stenosis, thus shortening the procedure, reducing trauma, and reducing procedure cost.

After an obstruction is cleared, it is possible to decrease the circumference of the coil by elongation and easily withdraw the coil and associated cather from the vessel.

The coil tip is rotated at a desired speed during its passage through the stenosis. Once the obstruction is cleared, the coil is returned to its original smaller diameter and may be easily withdrawn from the vessel.

According to alternative embodiments of the invention described and claimed herein, there is provided a device which combines the benefits of an atherectomy procedure with the capabilities of a balloon angioplasty procedure with but a single trip or entry into the occluded vessel, in situations where the use of such a device is desired or required. The device of the present invention thus saves the time and expense, and avoids the increased difficulty or risk, of having to perform two separate procedures, that is, the atherectomy procedure followed by a separate balloon angioplasty procedure, in those cases where, for example, tacking of dissected tissue is desired or where the physician is reluctant to use a rotatable burr of sufficient size to create the targeted opening.

In alternative embodiments of the present invention there is thus provided a combined atherectomy and balloon angioplasty device having a rotatable ablator tip of either a fixed or a variable diameter, and an angioplasty balloon disposed proximally of and spaced a relatively small distance from the ablator tip. The angioplasty balloon is affixed to the drive coil which drives the ablator tip, and may be moved back and forth in a longitudinal axial direction along with the drive coil in order to manipulate the balloon into position for performing the angioplasty procedure. The balloon is selectively inflatable with a fluid, such as a saline solution, to a diameter which may be greater than that used for the atherectomy procedure in order to expand the vessel beyond the maximum diameter at which the atherectomy procedure is performed, or to tack a flap of tissue back to the vessel wall. When the angioplasty balloon is inflated, the rotation of the drive coil is halted or disabled. Thus, it can be seen that with a device according to these alternative embodiments of the present invention, during any one "trip" into the occluded vessel, the physician can perform an atherectomy procedure alone, or a combination of an atherectomy procedure and a balloon angioplasty procedure, in order to produce the best result for the patient.

These and various other characteristics and advantages of the present invention will become readily apparent to those skilled in the art upon reading the following detailed description.

BRIEF DESCRIPTION OF THE DRAWINGS

For a detailed description of the preferred embodiments of the invention, reference will now be made to the accompanying drawings, wherein.

DETAILED DESCRIPTION OF THE PREFERRED EMBODIMENTS OF THE INVENTION

The drawings are illustrative of the apparatus of the present invention used for removing an obstruction from a vessel. The embodiments described are exemplary only, and can be modified in the practice of the invention.

Figure 1:
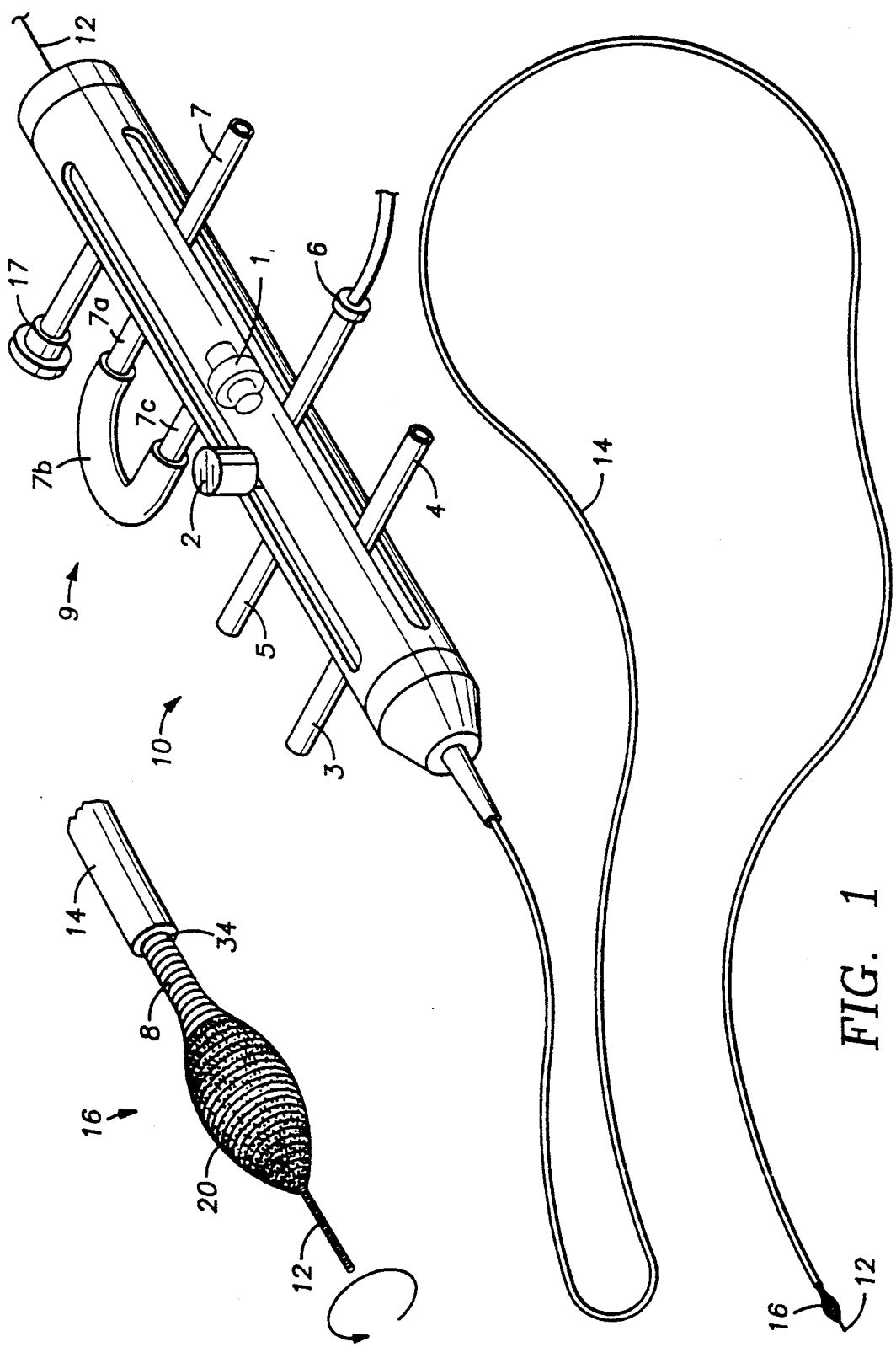
FIG. 1 is a schematic representation of the apparatus of the present invention with its drive-control unit at its proximal end and the drive coil, expandable tip, and guide wire disposed within the flexible outer catheter which surrounds the drive coil.

FIG. 1 is a schematic representation of one type of system 10 adapted for use with some of the preferred embodiments of the adjustable tip atherectomy device of the invention. A drive-control unit 9 is attached to one end of a flexible catheter 14 which surrounds a drive shaft coil 8. Drive shaft coil 8 is adapted for high speed rotation within the catheter 14. Flexible catheter 14 is made of a suitable biocompatible material capable of withstanding the heat of friction generated when drive shaft coil 8 is rotated at high speed. Speeds of rotation of drive shaft coil 8 within flexible catheter 14 of about 100,000 to 300,000 revolutions per minute are contemplated for the present invention, which speeds may be generated, for example, by means of a conventional compressed air turbine or the like. An expandable, adjustable diameter coil tip 16 is attached to drive shaft coil 8 at its distal end. The proximal end of the drive shaft coil 8 is attached to a torque drive device 1, such as the aforementioned compressed air turbine, which is centrally disposed within the drive-control unit 9. Actuation of the torque drive device 1 drives the drive shaft coil 8 which in turn rotates the expandable, adjustable diameter coil tip 16. The drive shaft coil 8 is preferably of a helically wound hollow wire configuration and is made of stainless steel or another suitable material capable of transmitting torque to drive the coil tip 16 at speeds as high as those referred to above which are contemplated for the present invention. Such helical coils with diameters as small as 0.032 inches have been used in the past for such high speed rotational torque transmission applications. Flexible catheter 14 assists in containing the forces acting on and transmitted by the drive shaft coil 8, and protects the body's intervening vasculature from injury or trauma during rotation of the drive shaft.

An air inlet port 7 of drive-control unit 9 accepts air from a conventional air pressure control unit (not shown) commonly found in hospital settings and well known to those skilled in the present art. Air at controlled pressure is applied momentarily and for the desired duration of tip rotation. The pressurized air passes through the inlet port 7 and communicates to the torque drive device inlet port 7c via air outlet port 7a and connecting tube 7b. Rotational speed is monitored by a conventional tachometer connected to tachometer cable connector 6 of drive-control unit 9. The air pressure control unit (not shown) may be adjusted to result in application of the desired air pressure to the turbine or the like to effect the desired tip rotational speed.

Drive-control unit 9 also includes several ports which communicate to various lumens of the overall atherectomy device of the present invention. Generally, the various lumens permit the injection through the device of fluids, such as medication, hydraulic actuation fluids for actuating the means for adjusting the expandable tip 16 of the device, and cooling fluids for reducing friction heating during high speed rotation, as further described below. Cooling fluids, for example, are introduced into the flexible catheter 14 around the drive shaft coil 8 to bathe the coil 8 during rotation.

In practice it is necessary to visualize the stenotic obstruction to be treated by the device of the present invention. This is accomplished by the injection of a contrast medium and fluoroscopic visualization as is commonly practiced by those skilled in the art. The atherectomy device of the present invention permits the injection of a contrast medium through central lumen 64 and the annular space 34, FIG. 1 and FIG. 2, created between the outer surface of the drive shaft coil 8 and the inner surface of flexible outer catheter 14. Port 3 of drive-control unit 9 communicates with the annular space 34 and, in addition to serving as a means for contrast medium injection, may be used to inject cooling fluid during high speed rotation. Port 4 of drive-control unit 9 communicates with central lumen 64, shown in FIG. 2, and may be used for the injection of a contrast medium, medication, and other fluids through the central lumen 64.

Figure 2:
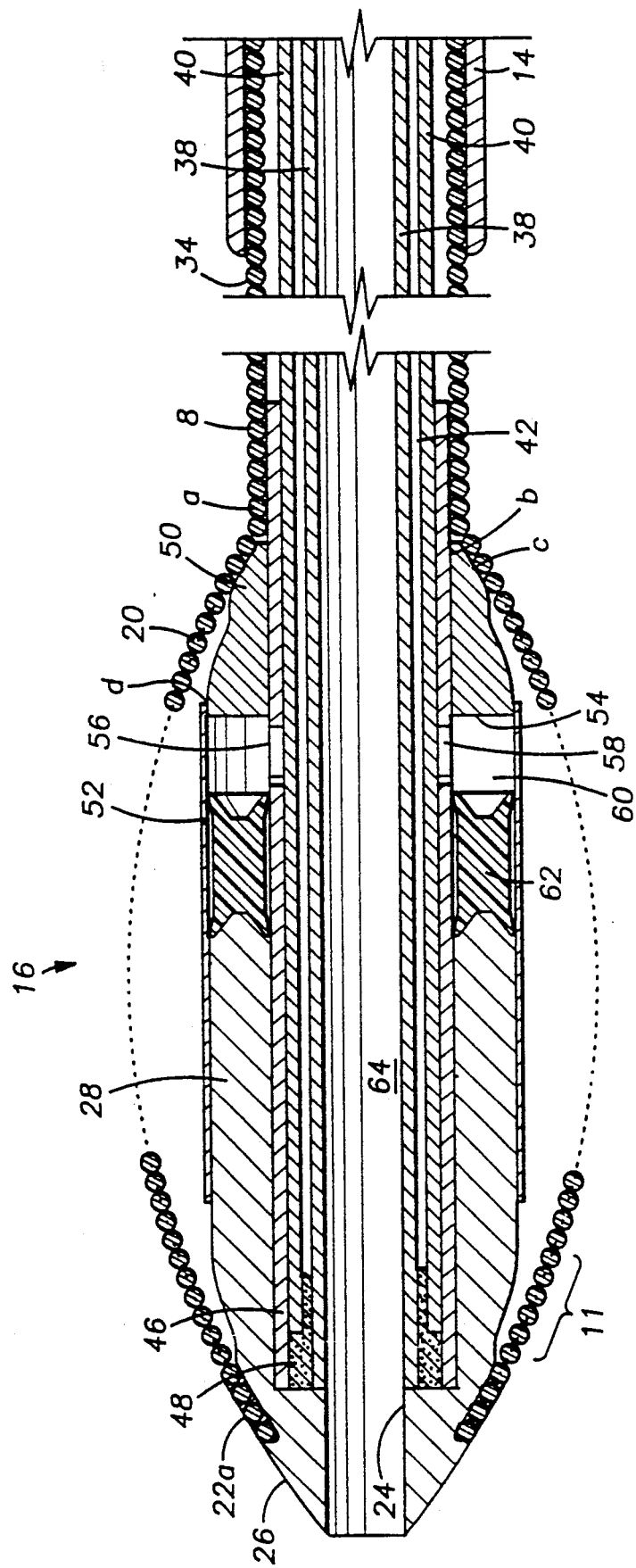
FIG. 2 is a length-wise cross sectional view of the expandable coil and the associated piston and inner catheter with the coil retracted and the coil circumference enlarged.

Referring to FIG. 2, it can be seen that central lumen 64 is created by a flexible catheter tube 38 which is disposed substantially concentrically and coaxially within a larger inner diameter flexible catheter tube 40. These concentrically and coaxially disposed inner catheters extend proximally within the passage created by the drive shaft coil 8 and extend beyond the proximal end of the drive shaft coil 8 within the drive-control unit 9. The concentric and coaxial disposition of flexible catheters 38 and 40 and the difference between the size of the outer diameter of catheter 38 and the inner diameter of catheter 40 creates an annular space lumen 42 which communicates to drive-control unit port 5, thus creating a passage for the purpose of activating the expanding means used to adjust the diameter of the ablating coil tip 16, as described further below.

The distal terminal ends of concentrically and coaxially disposed flexible catheters 38 and 40 are sealed by potting material 48 which serves to bond the tubes 38 and 40 together as well as to provide a distal seal for annular space lumen 42.

Central lumen 64 extends from the terminal distal end of tip 16 through drive-control unit 9 at its extreme proximal end. Thus the central lumen 64 can be used to guide the atherectomy device tip 16 of the present invention to a selected vessel obstruction by introduction over a prelocated guide wire 12, shown in FIG. 1.

The atherectomy device of the present invention is introduced into the body by way of the brachial or femoral artery, utilizing the Grunzig technique, which method is well known to those who practice in the area of catheterization. The device of the present invention minimizes damage to the vessel selected for catheter introduction. Normally, an introducer sheath is used to access the vessel at the point of introduction. Through the prepositioned introducer sheath is placed a guiding catheter and a guide wire appropriate for directing the atherectomy device of the present invention to the selected stenosis to be treated. The size, or diameter, of the introducer sheath and guiding catheter is determined by the size or diameter of the device to be introduced for treatment of the obstruction. Since existing atherectomy devices are of a fixed diameter, it is often necessary to introduce progressively larger diameter devices in order to fully clear a stenotic obstruction. This requires the use of introducer sheaths of a diameter sufficient to accept the larger diameter device, which results in greater vessel trauma at the point of vascular access. It is not uncommon, for example, to require use of introducer sheaths of up to a size 10 F (10 French) in order to accommodate the desired diameter, for example about 2.25 to 2.5 millimeters, of prior art atherectomy tip. Applicant has even used a larger size introducer sheath, e.g., of size 11 F (11 French), to accommodate a fixed diameter burr of about 2.75 to 3.0 millimeters, but to Applicant's knowledge, substantially no one else has used an introducer sheath so large as the 11 F and a burr of the corresponding large size diameter without the need for balloon assistance for practicing the prior art atherectomy technique described above. In addition, as noted previously, the larger diameter atherectomy devices of the prior art may cause increased vascular tissue trauma as they are guided to the obstruction to be treated, and also may disturb, in passing, other, smaller vascular obstructions not otherwise indicated for treatment.

The present invention, due to its variable, adjustable diameter tip 16 may be introduced by the technique just described but can employ an introducer sheath and guiding catheter of a diameter that is less than its maximum expanded diameter. For example, it is contemplated that an introducer sheath of a size 6 F, which is considerably smaller in diameter than the size 10 F, can be used effectively with the expandable abrading tip of the present invention, even when removing obstructions that would require a 10 F, 11 F, or larger size sheath according to prior art techniques. This results in decreased vessel trauma at the vessel access site and also in decreased vessel trauma en route to the obstruction, which features offer a distinct advantage over existing atherectomy devices. The device of the present invention minimizes or avoids this vessel trauma because it is introduced and guided into position for treatment in its minimal diameter configuration.

Figure 3:
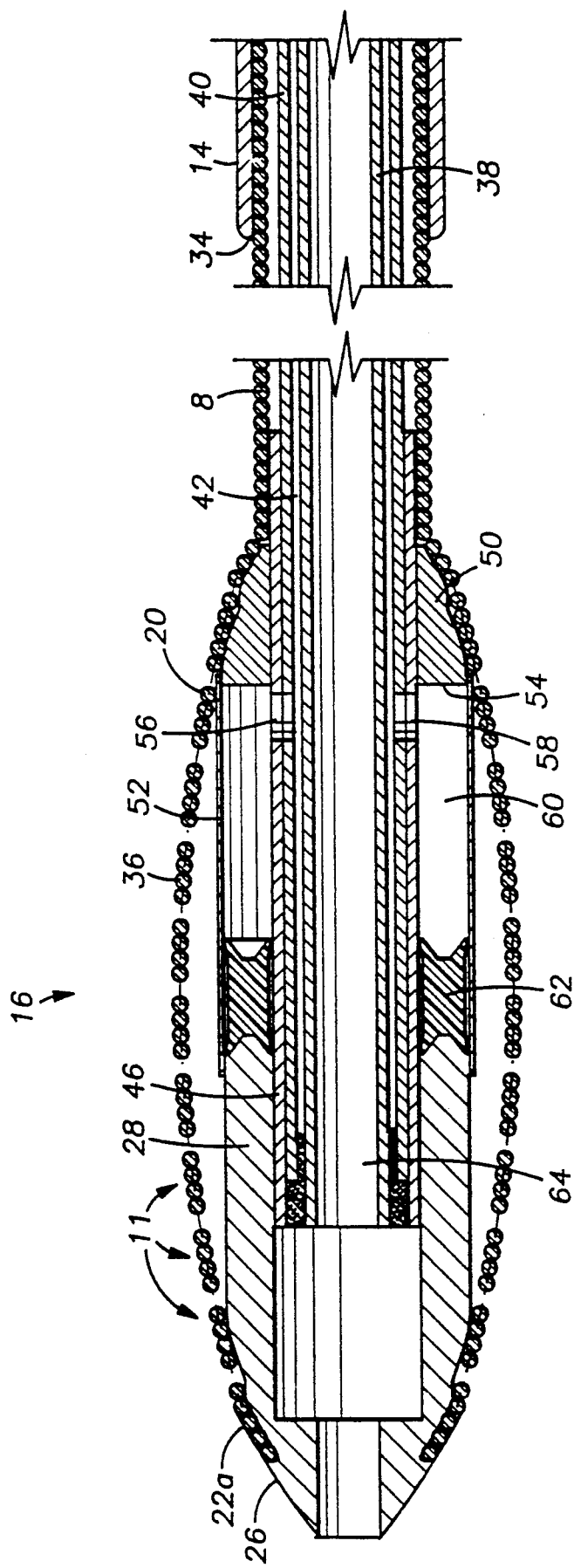
FIG. 3 is a length-wise cross sectional view of the coil of FIG. 2 in the elongated position with a smaller coil circumference.

Referring to FIGS. 2 and 3, the variable diameter feature of the abrading coil tip 16 of the invention will be described. FIG. 2 shows a piston means for one preferred embodiment of the dynamic variation of the abrading tip coil 20. FIG. 2 illustrates the abrading tip coil 20 in its maximum diameter condition and the activating means or piston in its deactivated condition. The piston is comprised of a proximal collar ring 50, a cylindrical piston inner sleeve 46, a cylindrical piston outer sleeve 52, a slidable piston seal ring 62, and a distal slidable piston collar 28 which also comprises the distalmost tapered abrading surface 26 of the device of the present invention.

The piston sleeves 46 and 52, the proximal collar 50, and the distal collar 28 are preferably made of stainless steel, but may be made of other materials suitable for the desired piston function and attachment described below.

Cylindrical piston inner sleeve 46 is attached to a number of the coil winds of drive shaft coil 8 at region "a" as well as to proximal collar 50 at region "b" by circumferential welding or the like. Outer piston sleeve 52 is circumferentially welded or the like to proximal collar 50 at region "d". Inner piston sleeve 46 is concentrically and coaxially disposed over flexible catheter tube 40 and bonded thereto to sealably fix the sleeve 46 around the flexible tube 40. The seal between inner piston sleeve 46 and flexible tube 40 is created by a tight slip fit between the members and by epoxy bonding or the like.

The distal piston collar 28 is slidably and rotationally free to move or telescope between inner piston sleeve 46 and outer piston sleeve 52. The slidable contacting surfaces of distal collar 28 and piston sleeves 46 and 52 may be deposited with a thin Teflon coating or the like to enhance the movement of distal collar 28 during piston function.

At the proximal termination of distal collar 28 and circumferentially disposed around inner piston sleeve 46 is slidable piston seal ring 62. Preferably made of Teflon or other suitable material, seal ring 62 is the primary piston "O" ring seal and is free to slide longitudinally axially between piston sleeves 46 and 52, thus creating a sliding seal between sleeves 46, 52.

Piston cavity 60 is an annular or circumferentially disposed, enclosed space bounded by the terminal distal face 54 of collar 50, the proximal terminal face of piston seal ring 62, the inner wall surface of sleeve 52, and the outer wall surface of sleeve 46.

Piston ports 56 and 58 access piston cavity 60. The ports 56, 58 are two, preferably, of a total of four piston ports that communicate through the wall of piston inner sleeve 46 and the wall of flexible tube catheter 40 to access annular space lumen 42.

Adjustable diameter, ovaloid shaped coils 20 of tip 16 are circumferentially disposed around the internal piston elements. The distal terminus of ovaloid coils 20 is attached to the piston distal collar at region 22a by circumferential welding or other suitable means. The distal attachment of coil 20 to distal collar 28 at region 22a is such that the attachment preferably forms a smooth continuation of the outer ovaloid surface of the tip 16. Thus, a smooth transition from the outer surface 26 of distal piston collar 28 to the coil 20 ovaloid surface is created.

Tightly wound ovaloid coil 20, by its attachment to distal piston collar 28 at region 22a and its attachment to proximal piston collar 50 at region "c", forms the piston's return spring.

As previously described, annular space lumen 42 communicates with port 5 of drive-control unit 9 and piston ports 56 and 58. Application of hydraulic pressure, or other suitable fluid pressure, at port 5 of drive-control unit 9 will transmit the necessary force to cause piston seal 62 to move distally and push slidable distal piston collar 28 in a forward or distal direction. As pressure at port 5 is increased, the major diameter of ovaloid coil 20 at the tip 16 decreases and the ovaloid outer shape lengthens or stretches to an increasingly right circular cylindrical configuration. As piston activation pressure increases, the ovaloid coil 20 stretches and unwinds under the pulling force exerted at region 22a by the distal movement of distal collar 28. The piston may be provided with a helical groove or the like, in which rides a radially outwardly projecting pin or the like disposed on the sleeve 46, to direct and channel the winding or unwinding movement of the coil winds as the piston is deactivated or activated, as the case may be.

FIG. 3 illustrates the effect of the piston activation at its maximum distal travel or movement. The ovaloid coil 20 shown in FIG. 3 comprises a quadrifilar coil which has been stretched and unwound in groups 36 of four winds per group when affected by the piston forces just described. Although a quadrifilar coil is shown, which coil stretches and unwinds also substantially as shown, other types or styles of coils, which stretch and unwind in other ways, may be used in the present invention.

The diameter of tip 16 can be varied from its maximum ovaloid diameter shown in FIG. 2 to its minimum elongated ovaloid diameter shown in FIG. 3. The dynamic diameter of the ovaloid tip 16 is a function of the piston activation pressure applied to piston cavity 60, and the return spring force of ovaloid coil 20. It is thus possible to select any desired tip diameter within the range bounded by the maximum and minimum diameters by selecting the appropriate piston activation pressure applied at port 5 of drive-control unit 9. The activation pressure can be set and monitored using standard gauges and pressure systems commonly used and well known to those of ordinary skill in the art.

Referring again to FIG. 1, there is shown on drive-control unit 9 a button 17 which serves as an air valve actuator to activate an air clamp which is centrally and proximally disposed within the drive-control unit 9. The air clamp is supplied by air from inlet port 7 and closes around and holds guide wire 12 in position at all times, except when the valve button is depressed. Thus the guide wire 12 is normally held during device rotation and released for advancement through the entire length of the atherectomy device.

The atherectomy device of the present invention will clear vascular stenoses by abrading or wearing away the stenotic material. The surface of the abrading tip 16 is deposited with particles, such as diamond dust 11, which may partially or totally cover the outer surface of ovaloid tip 16. The abrasive material surface may cover all or any portion, from the distalmost outer surface 26 of distal piston collar 28 to region "b" at the proximal termination of ovaloid tip 16.

The particle size of the abrading material 11 should be substantially uniform over the abrading surface of the tip. Particle diameter size should be in the range of about 10 to about 100 microns, with a preferred subrange of about 10 to about 20 microns. With abrading particles of about this size, rotated at the speeds contemplated for the present invention, the pieces of stenotic material abraded away will be about 5 to about 8 microns in diameter, which is less than the typical diameter of a red blood cell. At such a small particle size, the pieces of stenotic material abraded away can be disposed of naturally by the body through the capillary beds and there is no need for additional means of debris collection. Both soft and hard stenotic material may be removed by the cutting action of the tip 16.

Alternately, the abrading property of the surface of the tip 16 may be imparted by other methods, such as peening.

The tip 16 of the device of the present invention, unlike the tips of prior art devices, is preferably capable of abrading in both the forward and reverse progressions of the tip through a stenosis. This is due to the grit 11 preferably being deposited on both the leading and trailing slopes of the ovaloid tip 16.

Vascular recanalization of obstructions representing less than about 50% to 60% occlusion are not indicated. It has been found that the treatment for such occlusions by angioplasty or atherectomy more often aggravates the condition and accelerates the stenotic growth. In practice, those occlusions requiring treatment, the target stenoses, are not isolated, but rather are preceded by upstream and followed by downstream occlusions which preferentially should not be treated or should be bypassed by the treatment device.

Unlike existing atherectomy devices with fixed diameter ablators, the device of the present invention may be adjusted to its lower diameter and guided past and through non-target stenoses with reduced probability of aggravating these lesions.

Figure 4:
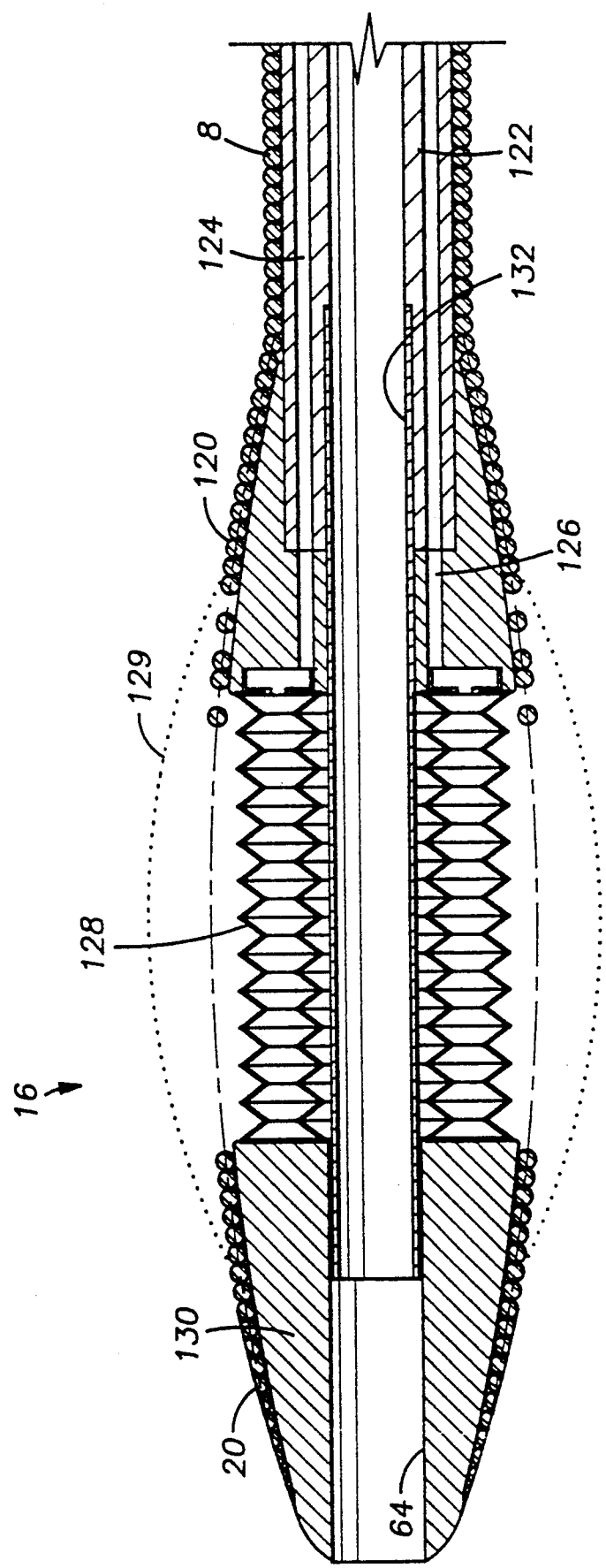
FIG. 4 is a length-wise cross sectional view of an alternative embodiment of the coil with a bellows associated with the coil for expansion.

Referring now to FIG. 4, there is shown a longitudinal cross sectional view of an alternative embodiment of the tip 16 of the atherectomy device of the present invention in which a bellows 128 is substituted for the piston as a means of ovaloid coil expansion. The bellows comprises a longitudinally expandable and contractible, hollow annular member having a plurality of accordion-like folds along its length. Bellows 128 is made of deposited nickel or other suitable thin walled material. Bellows 128 is attached at its proximal end to the distal face of a proximal collar 120, which in turn is attached to a plurality of winds of the coil 20 of tip 16 by circumferential welding or the like. A catheter tube 122 is sealably attached to the interior bore of the proximal end portion of collar 120. Catheter tube 122 preferably comprises a pair of concentrically and coaxially disposed flexible tubes forming an annular space lumen 124 therebetween. Catheter tube 122 is concentrically and coaxially disposed within drive shaft coil 8. Annular space lumen 124 communicates through passages 126 in collar 120 to the interior of bellows 128 at its proximal end. The distal end of bellows 128 is attached to the proximal face of a slidable distal tip collar 130. A plurality of winds of the coil 20 at its distal end are attached to the outer surface of the tip 130 by circumferential welding or the like. A metal guide tube 132 is attached within and to the distal end of the catheter tube 122, and projects therefrom through the bellows and into the central axial bore of the tip 130. The tip 130 is free to slide rotationally and longitudinally axially on the guide tube 132. Upon application of activation pressure, longitudinal expansion of the bellows 128 causes the tip coil 20 to stretch, reducing its circumference or diameter in a manner similar to that described in connection with the embodiment shown in FIGS. 2 and 3. Removal of the activation pressure will cause the bellows to contract, because of the spring effect associated with the metal bellows configuration. When the bellows is in its contracted state, the diameter of the ovaloid tip 16 is at its maximum, and when the bellows is in its expanded state, the diameter of the tip is at its minimum. FIG. 4 illustrates the bellows in its expanded state. The increased diameter of the coil when the bellows is in its contracted state is indicated in the central portion of the figure by the dotted lines 129.

Figure 5:
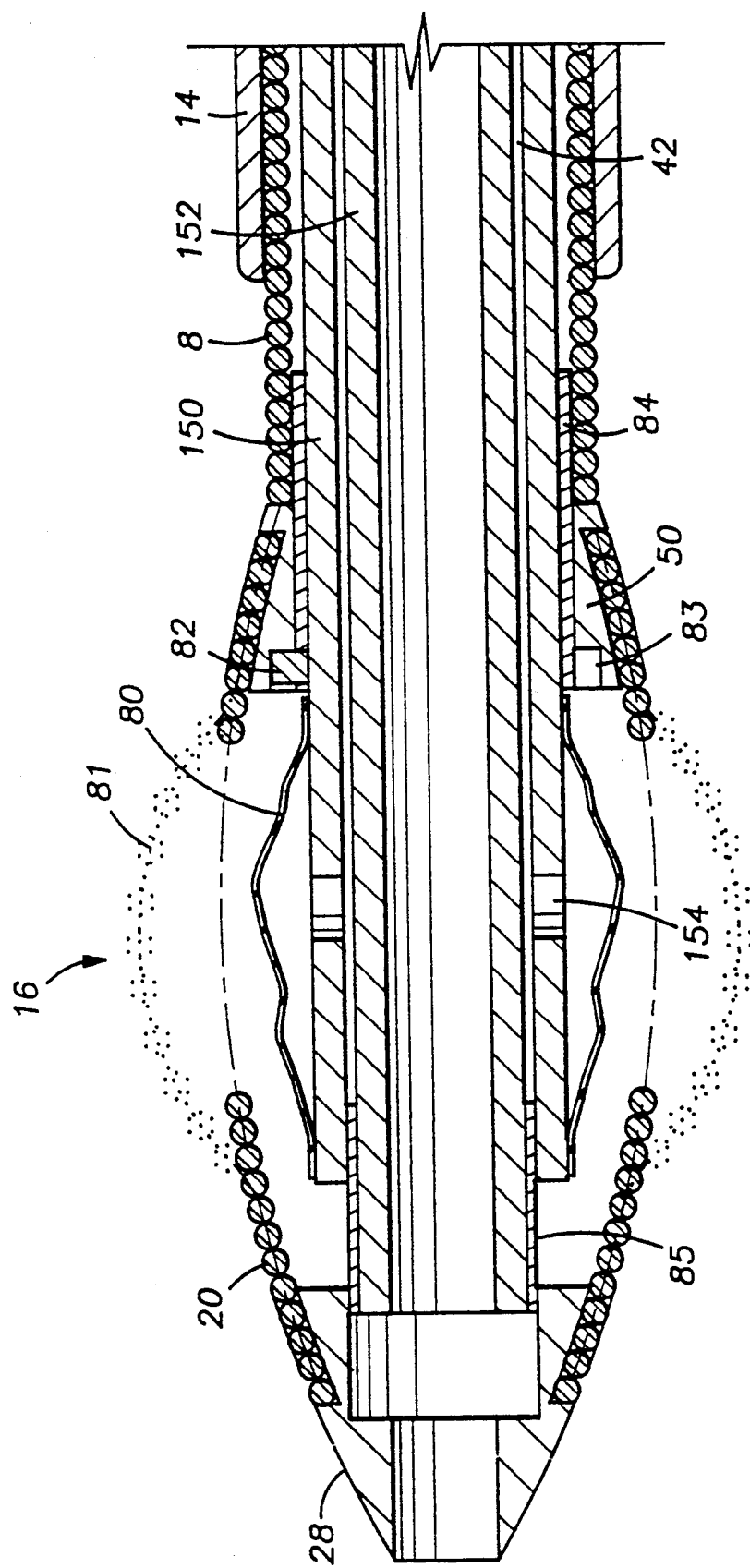
FIG. 5 is a length-wise cross sectional view of an alternative embodiment with an inflatable balloon used for coil expansion.

Referring to FIG. 5, there is shown a cross sectional view of an alternative embodiment of the tip 16 in which a high pressure balloon 80, such as those commonly used in angioplasty devices, is used as the tip coil expansion means. In this embodiment the tip 16 is normally in its minimum diameter condition. As in the previously described embodiments, the annular space lumen 42 conveys the pressure required to expand the balloon 80. As the balloon 80 expands, it expands the associated central portion of the tip coil 20. This results in a tip diameter increase that simultaneously changes the ovaloid shape of the tip 16 to a modified ovaloid shape having a compound ovaloid or distended central portion 81.

As seen in FIG. 5, this embodiment may incorporate a pin 82 which rides in a 350° slot 83 which is circumferentially disposed around the inner wall surface of a proximal collar 50. The pin is fixed to a proximal metal slide tube 84 by welding or the like. The proximal metal slide tube 84 is disposed around an outer catheter tube 150. The proximal collar 50 is rotationally free to move over the surface of proximal metal slide tube 84 and may rotate a total of 350°, at which time it engages the drive pin 82. The drive shaft coil 8 is weldably or otherwise attached to the proximal metal slide tube 84 and thus may drive the proximal collar 50 during high speed rotation. A distal collar 28 is weldably or otherwise attached to a plurality of winds of coil 20 at its distal end, and the proximal collar 50 is weldably or otherwise attached to a plurality of winds of coil 20 at its proximal end. A metal slide tube 85 is mounted around the distal end of an inner catheter tube 152, and is telescoped into a central axial counterbore in the proximal face of the distal collar 28. The metal slide tube 85 is sealably disposed between the catheter tubes 150, 152 and seals the distal ends of the tubes 150, 152. The lumen 42 between the catheter tubes 150, 152 communicates through ports 154 in the outer catheter tube 150 to the interior of balloon 80, which is mounted on the outer surface of the outer catheter tube 150. Air is introduced through the ports 154 to inflate the balloon 80. The distal collar tip 28 is free to slide longitudinally axially and rotationally over the surface of metal slide tube 85, and collar 50 is free to rotate over the surface of its associated slide tube 84. Thus the coil 20 of tip 16 may unwind and wind as the coil expands and contracts, as the case may be, under the action of the balloon 80. The balloon 80 at its maximum inflation forces the center of the ovaloid to its maximum diameter. Removing the air pressure from the balloon causes it to deflate, allowing the coil to return to its normal, reduced diameter state.

Figure 6:
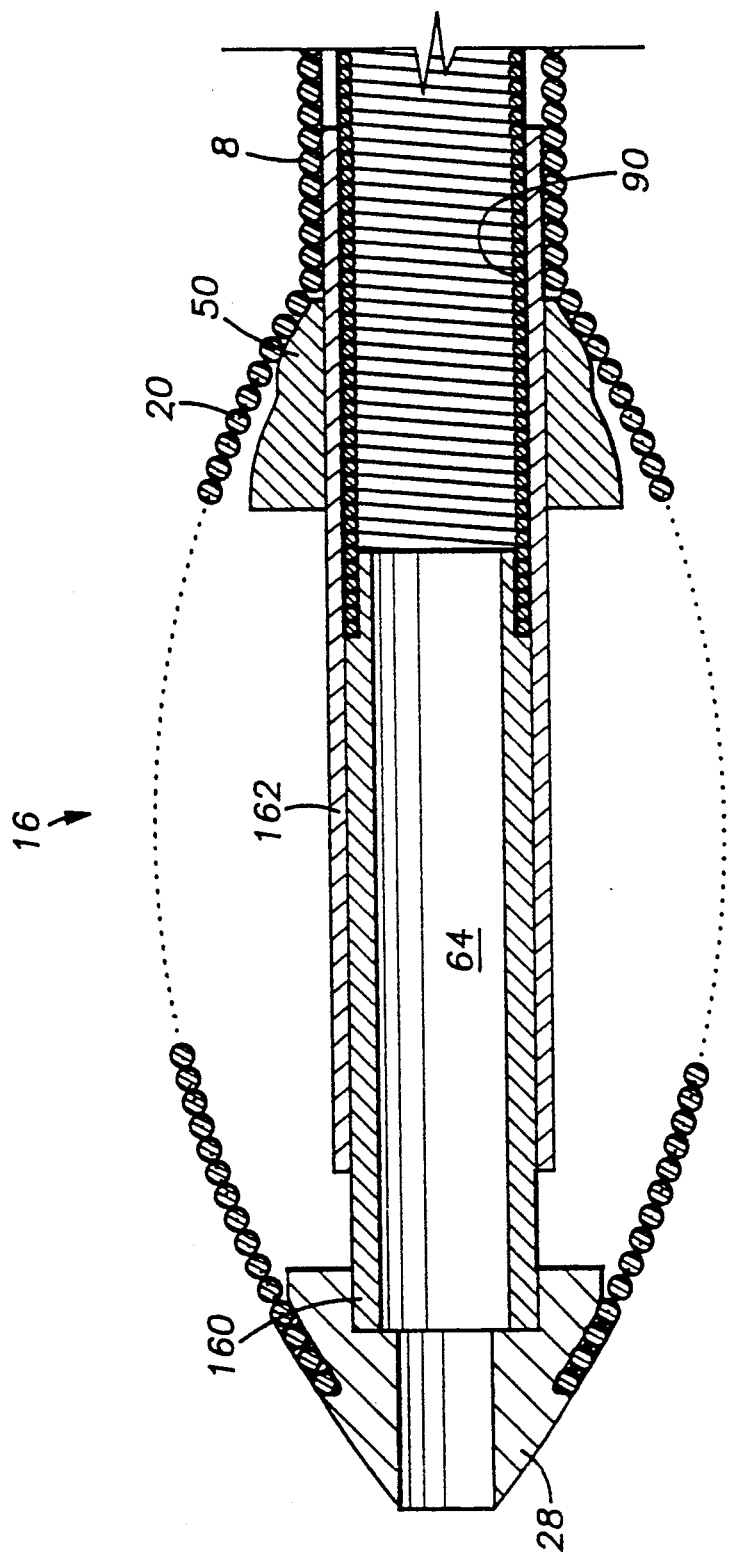
FIG. 6 is a length-wise cross sectional view of an alternative embodiment with a pair of concentrically and coaxially disposed, telescopingly slidable sleeves disposed within the coil and cooperable to effect coil expansion.

FIG. 6 is a cross sectional view of an alternative embodiment in which a second helical coil 90 is coaxially and centrally disposed within the drive shaft coil 8. The innermost coil 90 is free to slide within the drive shaft coil 8 and extends through the entire length of the device. A pair of such coils as manufactured by Lake Region Manufacturing Company, Inc. of Chaska, Minn., may be found suitable for use in this embodiment, but other or equivalent coils can of course be used. The distal end of the inner coil 90 is attached to the distal tip collar 28 through an inner slide sleeve 160. The ovaloid tip 16 coil 20 is attached to the distal and proximal collars 28, 50 as previously described. An outer slide sleeve 162 is telescoped over the inner slide sleeve 160 and is disposed at its proximal end within the central axial bore of the proximal collar 50. The inner slide sleeve 160 is free to telescope longitudinally axially within, and to rotate within, the outer slide sleeve 162.

The tip 16 of FIG. 6 is normally in its maximum diameter condition and is caused to reduce its diameter by the longitudinal movement of the inner coil 90 within the drive shaft coil 8 in a distal direction. When the inner coil 90 is pushed and/or rotated distally within the drive shaft coil 8 the distal tip collar 28 moves forward, in relation to proximal collar 50 and causes the tip coil 20 to stretch. Thus the tip diameter may be reduced. The tip 16 diameter in this embodiment is a function of the longitudinal displacement of the distal collar 28 with respect to the proximal collar 50. The tip coil 20 for this embodiment may be a continuation of the drive shaft coil 8, as shown in FIG. 2, or an individual coil segment, as shown in FIG. 5.

Alternatively, the coil 20 of ovaloid tip 16 may be replaced by a deposited metal ovaloid such as nickel, preferably having a wall-thickness of less than 0.002 inches. Further, the coil feature of the deposited metal tip may be cut into the previously deposited ovaloid shape such that the coil ribbons at the center, or apex, of the ovaloid are widest and decrease in width as the ovaloid slope descends to the distal and proximal minor ovaloid diameters. There may be one helix, or a plurality of adjacent helices, comprising the coil. The deposited metal coil alternative presents what may be described as a "lemon peel" feature. An illustration of such an embodiment is shown, for example, in FIG. 7.

Figure 8:
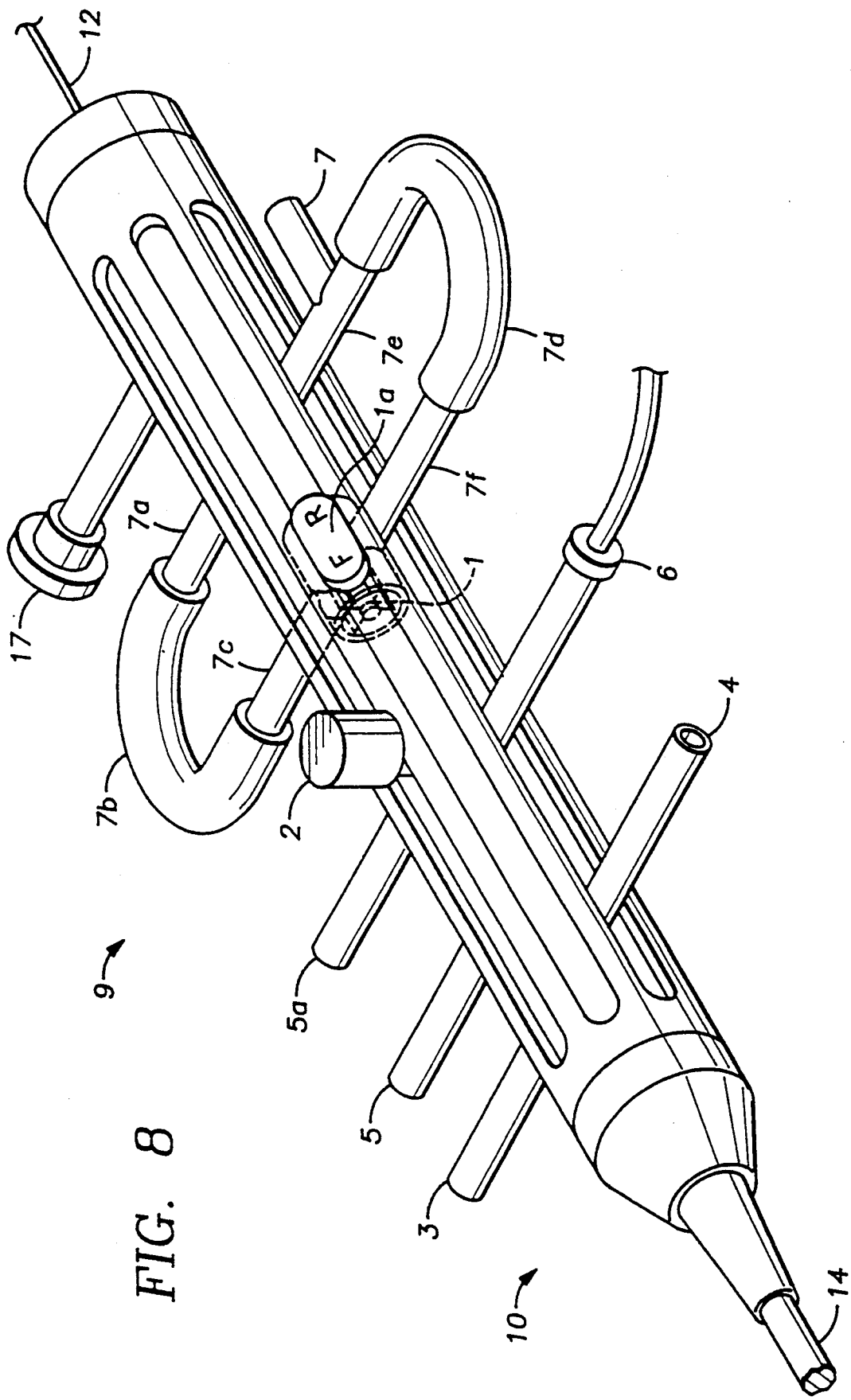
FIG. 8 is an enlarged pictorial/schematic view of a drive-control unit for an alternative embodiment of the present invention employing an angioplasty balloon along with the rotatable atherectomy tip. The drive-control unit of FIG. 8 is also illustrated as being equipped to produce rotation of the atherectomy tip in either a clockwise or a counterclockwise direction.

Referring now to FIGS. 8-11, there are shown alternative embodiments of the invention comprising combined atherectomy and balloon angioplasty devices, and a type of drive-control unit which may be employed with such alternative embodiments. FIG. 8 is illustrative of a type of system 10 adapted for use with the preferred embodiments of the invention shown in FIGS. 9-11. For ease of reference, parts of the embodiments of FIGS. 8-11 which are substantially like parts of the other embodiments described above, are given the same reference numerals. The drive-control unit 10 of FIG. 8 is similar to the drive-control unit of FIG. 1, with the following being the primary differences. The air supply inlet tube 7 incorporates tube 7e, flexible plastic tube 7d, and tube 7f. Rotatable drive turbine 1 will accept air inputs from tube 7c and from tube 7f. A turbine valve switch 1a is disposed on the drive-control unit of FIG. 8, in communication with the drive turbine 1, as a means for selecting a forward (e.g., counterclockwise, designated by the "F") or a reverse (e.g., clockwise, designated by the "R") tip rotation. As stated previously, air is supplied into inlet tube 7 at a regulated pressure and communicates to the turbine 1, which is disposed in the drive-control unit. If the air is directed to tube 7a, flexible plastic tube 7b, and tube 7c to one side of the turbine blades, they will rotate in one direction, e.g., forward, and if directed to tube 7e, flexible plastic tube 7d, and tube 7f to the opposite sides of the turbine blades, they will rotate in the opposite direction, e.g., in reverse. A valve which is disposed about the turbine alternately shuts off the flow of air through tube 7f or tube 7c to one side or the other of the turbine blades, simultaneously opening up the flow of air through the other of tubes 7f and 7c, thus permitting the operation of the rotatable tip in the desired direction. The ability of the tip to rotate in both a clockwise and a counterclockwise direction provides the physician with increased flexibility in carrying out the procedures. Inflation of the angioplasty balloon 200 (FIGS. 9-11) is effected through a tube 5a of drive-control unit 10 of FIG. 8. Inflation of balloon 200 is accomplished through application of hydraulic pressure, using a saline solution or other acceptable fluid as the pressure fluid, through the balloon inlet tube 5a. Conventional balloon pressure regulating gauges, such as gauged syringes, may be connected to the balloon inlet tube 5a to control balloon inflation. Balloon inflation pressure is communicated to the balloon via annular lumen 206, shown in FIG. 11, which is continuous with balloon inlet tube 5a.

Figure 9:
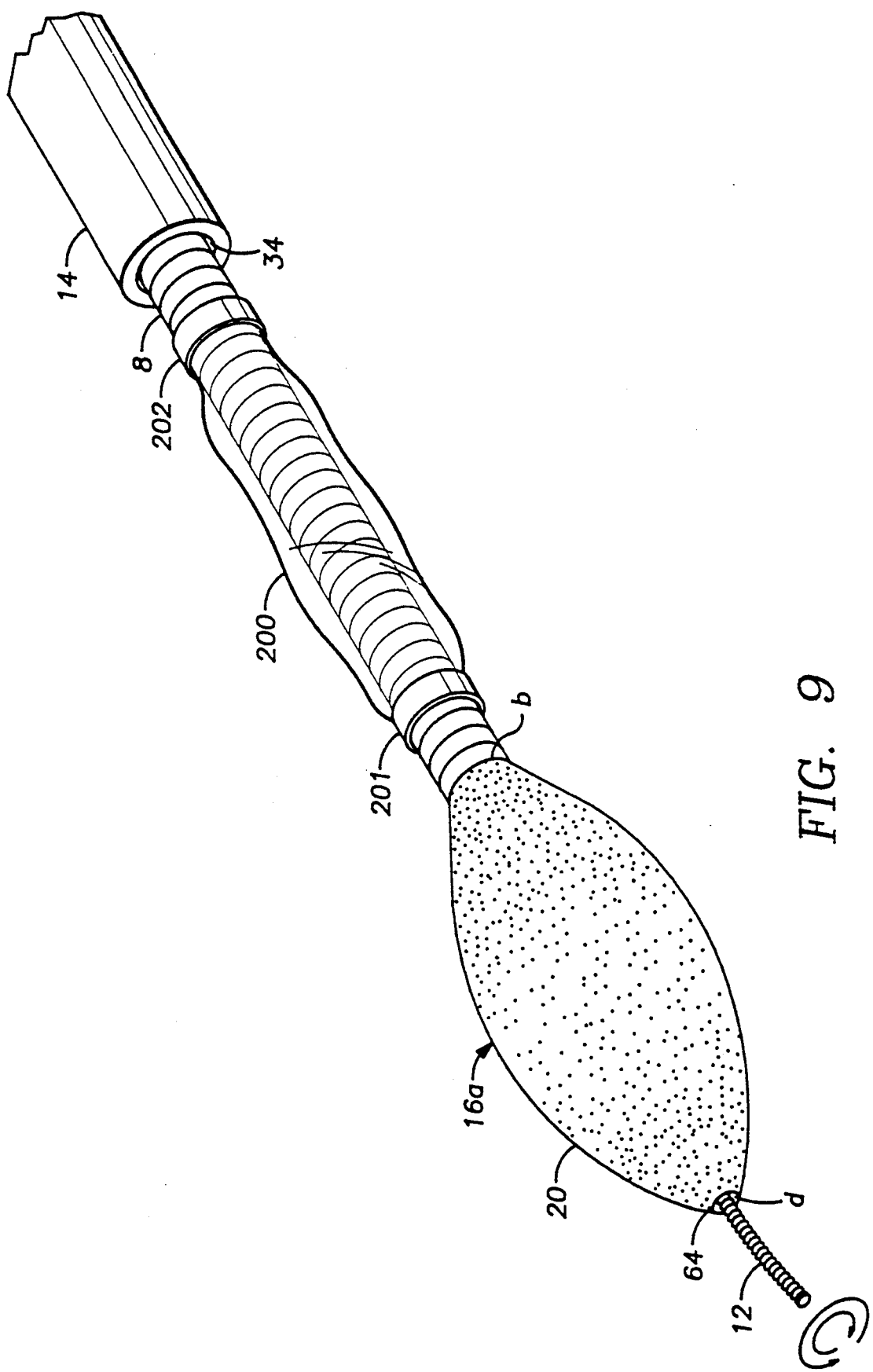
FIG. 9 is an enlarged pictorial view of an alternative embodiment of the present invention employing an angioplasty balloon along with a fixed diameter rotatable ablator tip, which is adapted for use with the drive-control unit of FIG. 8.

Referring particularly to FIG. 9, there is shown an embodiment of the combined atherectomy and balloon angioplasty device of the invention, which employs a fixed diameter rotatable ablator tip 16a. The oval tip 16a is hollow and has a wall thickness in a range of, for example, about 0.001 inches to about 0.003 inches, or the like. The oval tip 16a may be made by, for example, the metal deposition or hydroforming methods, or other suitable thin-walled member forming methods. The tip 16a has an abrading or "sanding" surface which may comprise a covering of a diamond dust material 20, or it may comprise an abrading surface produced by peening or other metal upsetting methods.

Hollow tip 6a includes a thin-walled, tubular metal member (not shown) centrally and axially disposed therewithin. The distal ends of the tip 16a and its centrally disposed tube are attached, as by welding, at region d. The proximal ends of the tubular central member and the oval tip 16a are attached, as by welding, at region b, and the drive shaft coil 8 is attached, again as by welding, to a portion of the thin-walled tubular metal member which projects proximally from the point of welding at region b.

An angioplasty balloon 200 is attached to the drive shaft coil 8. The distal end of balloon 200 is disposed proximal to the oval tip 16a and is attached by means of a flexible adhesive, such as urethane-based epoxy or the like, and a distal retaining ring marker 201 which is swaged over and disposed circumferentially about the distal attachment of the balloon to the drive shaft coil. The proximal end of the balloon is similarly attached to the drive shaft coil 8 at a point distal to the flexible catheter tube 14, and includes a proximal retaining ring marker 202.

The balloon retaining rings 201, 202 are preferably made of a material such as a platinum-iridium alloy or the like. In addition to assisting in balloon affixation, rings 201, 202 serve as markers to enhance fluoroscopic visualization and facilitate balloon placement at the desired site.

Balloon 200 may be made of PE, nylon, or other material as commonly found in balloon angioplasty catheters. The axial length of the balloon is preferably in the range of lengths of conventional angioplasty balloons, but may be provided in additional or different or varying lengths that more adequately respond to the combined application of atherectomy and angioplasty in a single procedure, as may apply to coronary or peripheral procedures. The balloon inflated diameters will be provided in a range of sizes for a given size tip 16a to accommodate the specific procedure requirements, as is common in conventional angioplasty procedures.

The relationship between the proximal end of the balloon 200 at ring 202 and the distal end of the catheter tube 14 is preferably such that when the drive shaft coil 8 is drawn fully into the catheter tube 14, as by retraction of the knob 2 of the drive-control unit, the retaining ring 202 does not enter the lumen 34 of the catheter tube. If, however, the balloon 200 were to be drawn into the catheter tube 14, the rotational drive to the device will be disabled, as by shunting the air supply away from the rotational drive means as ring 202 approaches closely the distal end of catheter 14, to prevent rotation of the balloon within the tube 14 and possible damage to the balloon.

Figure 7:
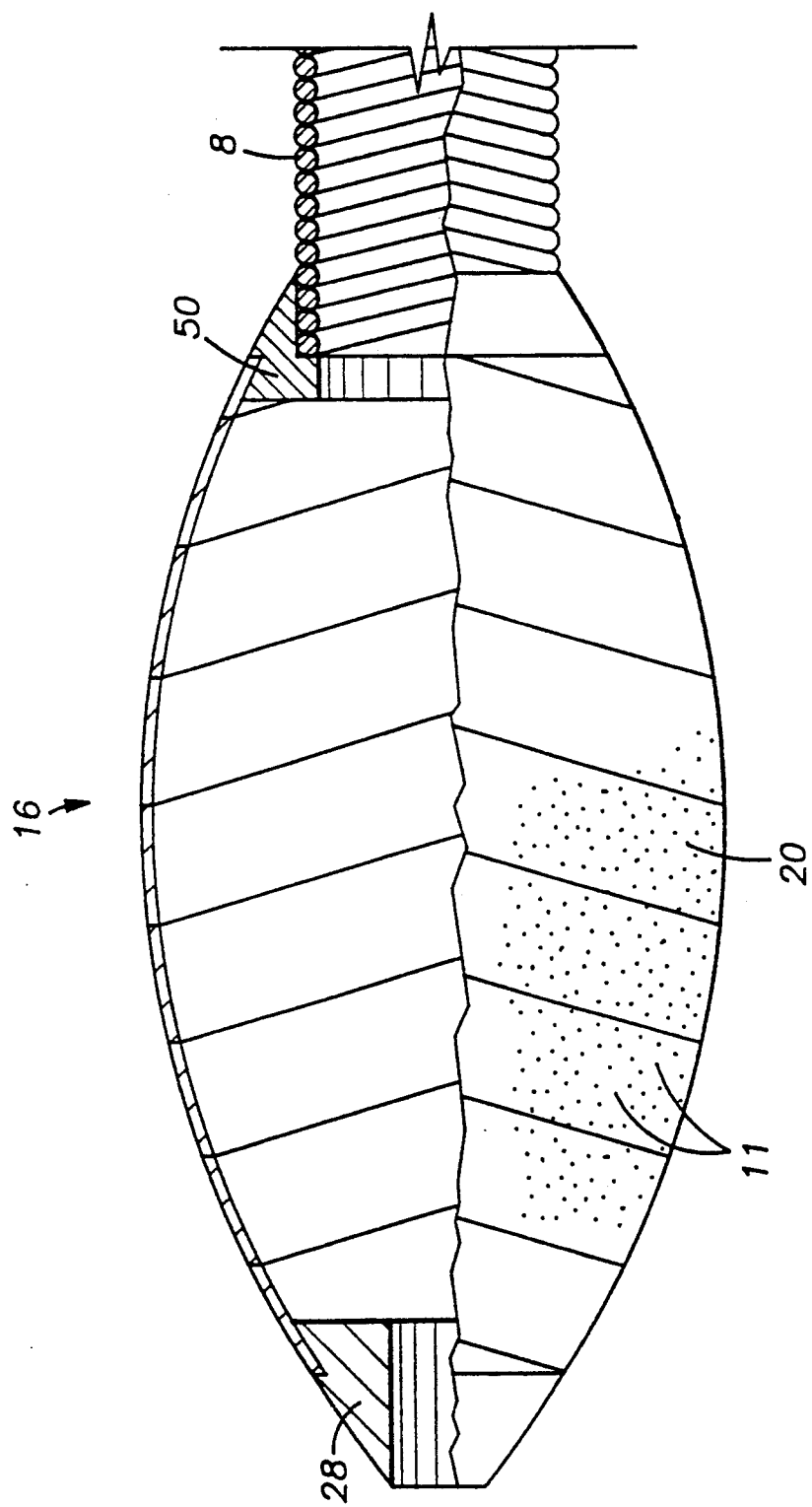
FIG. 7 is a length-wise cross sectional view of an alternative embodiment of the expandable coil wherein the coil comprises a helically wound ribbon-like metal strip.
Figure 10:
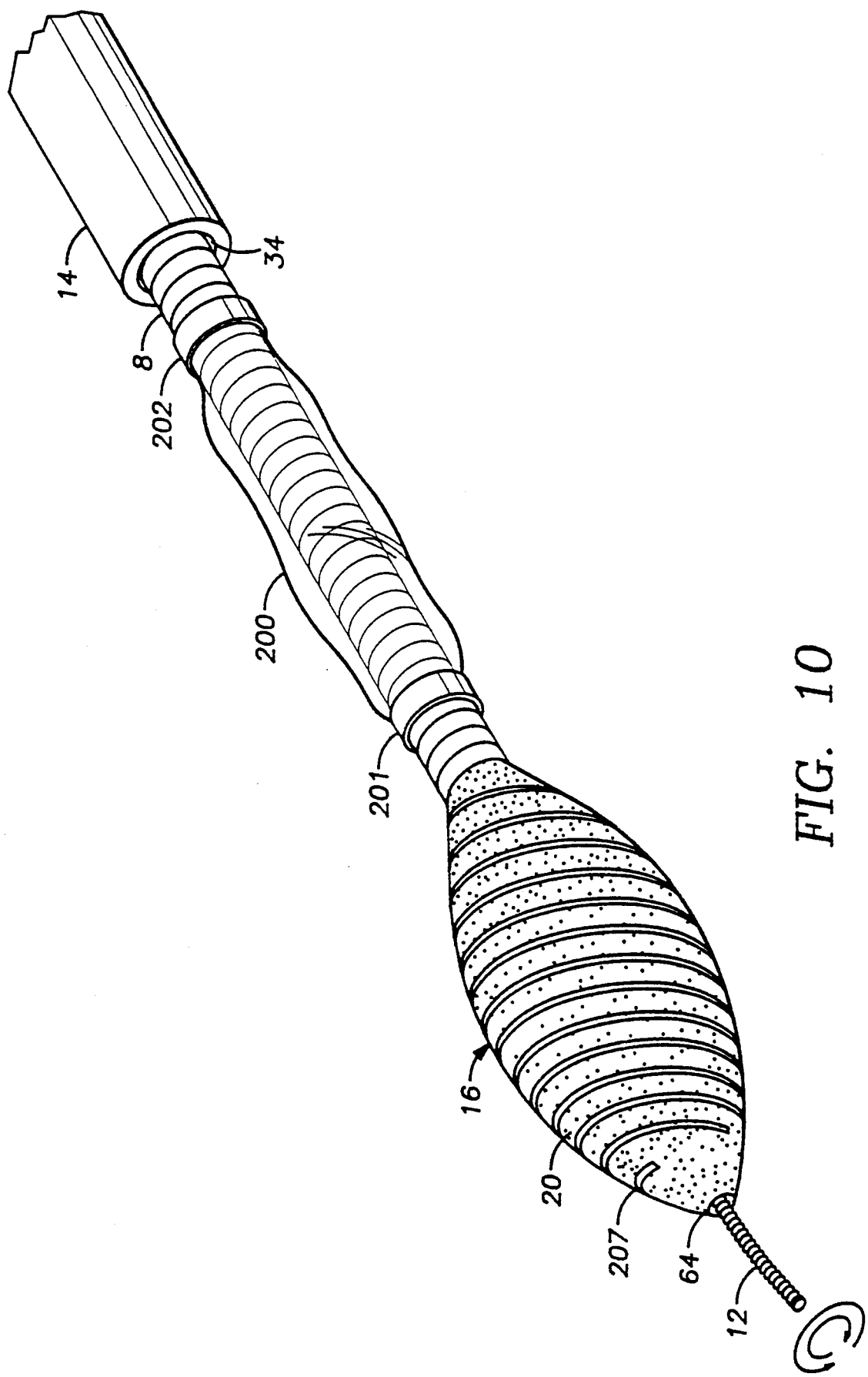
FIG. 10 is an enlarged pictorial view of another alternative embodiment of the present invention employing an angioplasty balloon along with an expandable diameter rotatable ablator tip, which is also adapted for use with the drive-control unit of FIG. 8.
Figure 11:
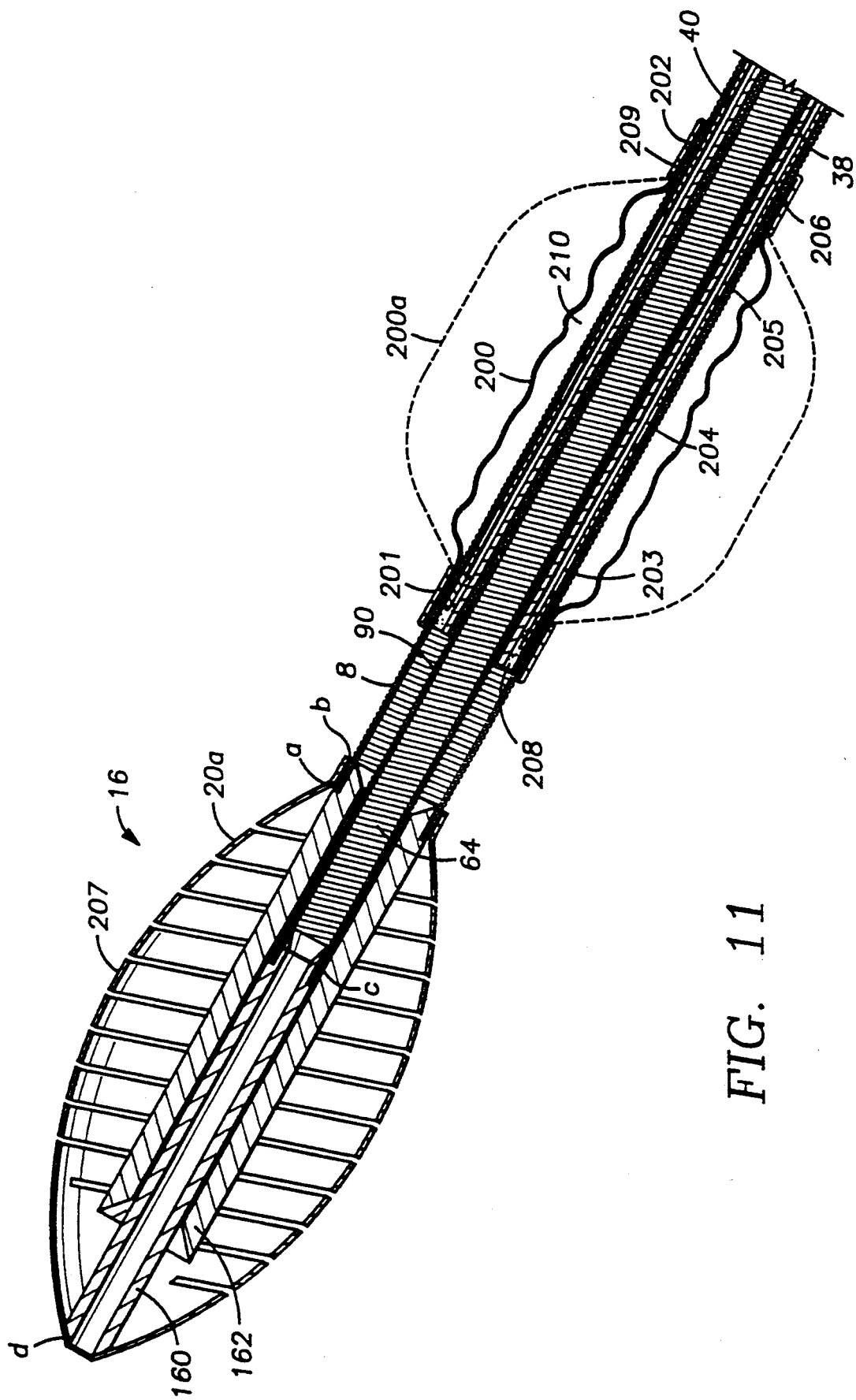
FIG. 11 is an enlarged, length-wise cross sectional view of the combined atherectomy tip/angioplasty balloon embodiment of FIG. 10.

Referring particularly to FIGS. 10 and 11, there is shown an embodiment of the combined atherectomy and balloon angioplasty device of the invention, which employs a variable diameter rotatable ablator tip 16. Variable diameter tip 16 may be formed of a coil having one continuous strand wound into a helix, or a plurality of strands wound into a plurality of intertwined helices, such as the quadrifilar coil shown in FIG. 3, or it may take the form of a deposited metal coil such as is shown in FIG. 7, or it may take on other suitable coil shapes as stated earlier. For illustrative purposes, and not by way of limitation, the tip 16 for this embodiment is shown and described as the deposited metal tip. Tip 16 shown in FIGS. 10 and 11 is similar to the tip 16a, except that this version of the hollow oval tip is configured into a ribbon spring. Slits 207 may be cut through the thin wall of the oval tip 16 by laser, electron beam, chemical erosion, electro-etching, or other suitable method. The abrading tip 16 is formed into an oval spring by virtue of the slits 207, which may be a single spiral slit or a plurality of intertwined slits. The spring oval tip 16 thus formed is capable of stretching and rotating along its center axis. When stretched and rotated, the spring oval tip 16 will elongate and its maximum diameter will be reduced in proportion to the extent of elongation. Thus, the tip 16 may be varied in diameter and length. Tip 16 has an abrading surface like that, for example, on tip 16a.

An angioplasty balloon 200 is disposed proximally to the tip 16 of FIGS. 10, 11. Balloon 200 of this embodiment is also disposed on the drive shaft coil 8 between the oval spring tip 16 and the distal end of the catheter 14. Balloon 200 preferably has a length and a maximum diameter comparable to the length and maximum diameter referred to above for the balloon of the embodiment of FIG. 9.

Centrally disposed within the spring ovaloid abrading tip 16 are tubular metal sleeves 160 and 162. The innermost sleeve 160 is attached, as by welding, to the distal end of the thin-walled ovaloid tip 16 at region d. Sleeve 162 is telescopingly disposed about sleeve 160. The sleeves 160, 162 are free to slide longitudinally axially and to rotate with respect to one another, in "trombone" fashion, with sleeve 160 being slidable within sleeve 162.

Drive shaft coil 8 is attached, as by welding, to the proximal end of sleeve 162 at the region defined between points a and b. The proximal end of the spring ovaloid abrading tip 16 is attached, as by welding, to the drive shaft coil 8 and sleeve 162 at the region defined by point b.

Multi-filar wire coil 90 is centrally disposed within the sleeve 162 and the innermost flexible plastic catheter tube 38. Wire coil 90 extends through the entire length of the catheter and the drive-control unit 9. The sleeve 160 is attached, as by welding, to the distal end of the wire coil 90 at the region defined by point c. The tip 16 of FIG. 11 is normally in its maximum diameter condition and is caused to reduce its diameter by the distal longitudinal movement of the inner coil 90 with respect to the drive shaft coil 8. When the inner coil 90 is pushed and/or rotated distally with respect to the drive shaft coil 8, the tip 16 is caused to elongate or stretch axially. Thus the tip diameter is reduced. The diameter of tip 16 in this embodiment is a function of the longitudinal displacement between the distal end of the tip at point d, and the proximal end of the tip at point b. Balloon retaining ring 201 is disposed proximal to the weldment region b. The distance between the weldment region b and the distal end of the ring 201 is such that the drive shaft coil 8 is allowed to flex over its length between the balloon and oval tip 16.

Coaxially disposed within the drive shaft coil 8 are flexible catheter tubes 38, 40. The catheter tubes form an annular lumen 206 that serves as the inflation lumen for the balloon 200. A similar inflation lumen is provided for the embodiment of FIG. 9. The annular lumen created by the tubes 38, 40 extends from its extreme distal end in the region of epoxy potting material 208 to a point within the drive-control unit 9 that terminates in fluid communication with balloon inflation tube 5a. A plurality of side ports or holes 203, 204, and 205 through the wall of catheter tube 40, within the balloon 200 and between the sealed end attachment points of the balloon to the drive shaft coil, serve to communicate pressured inflation fluid from the lumen 206 to the interior 210 of balloon 200. At the distal ends of the balloon 200 and the catheter tubes 38, 40, epoxy potting material 208 serves to seal the distal end of the annular lumen 206. The potting material also serves to attach the drive shaft coil to the coaxially disposed catheter tubes, the balloon, and the distal retaining ring 201. Similarly, epoxy potting material 209 serves to seal the proximal end of the balloon 200 at ring 202 and to attach it to the drive shaft coil and the outer surface of the catheter tube 40.

When inflation pressure, as by a saline solution or the like, is applied to balloon inflation tube 5a, the pressure is transmitted through the annular lumen 206, through the side ports 203, 204, 205, and passes through the spaces between the drive shaft coil windings. This inflation pressure is thus applied to the interior 210 of the balloon to cause inflation. When fully inflated, the balloon expands to a diameter suitable to accomplish the objectives of the procedure.

Thus, it can be seen that with either the embodiment of FIG. 9 or that of FIG. 10 and 11, during any one trip into the occluded vessel, the physician can perform an atherectomy procedure alone with fixed diameter tip 16a or variable diameter tip 16, or a combination of an atherectomy procedure with a balloon angioplasty procedure, i.e., a fixed diameter atherectomy procedure using tip 16a combined with a balloon angioplasty procedure using balloon 200, or a variable diameter atherectomy procedure using tip 16 combined with a balloon angioplasty procedure using balloon 200, in order to produce the best result for the patient. It should be noted, however, as persons skilled in the art should well know, that the atherectomy procedure and the balloon angioplasty procedure should not be performed simultaneously.

While preferred embodiments of the invention have been described, various modifications can be made to the preferred embodiments without departing from the principles of the present invention.

We claim:

1. An apparatus for treating an obstruction in a vessel, comprising:
   a coil;
   said coil being capable of elongation thereby reducing the circumference as said coil is elongated;
   means for selectively elongating said coil;
   means for introducing said coil inside a vessel proximate to an obstruction;
   said coil having an abrasive surface covering at least part of its outer surface;
   means for selectively rotating said coil;
   an angioplasty balloon disposed proximal to said coil; and
   means for selectively inflating said balloon.

2. An apparatus for treating an obstruction in a vessel according to claim 1, wherein said means for selectively rotating said coil includes a rotatable drive shaft in engagement with said coil, and wherein said angioplasty balloon is sealingly mounted around said drive shaft.

3. An apparatus for treating an obstruction in a vessel according to claim 2, wherein said drive shaft comprises an elongate tubular drive coil.

4. An apparatus for treating an obstruction in a vessel according to claim 3, wherein said means for selectively inflating said balloon comprises a pair of coaxial, radially spaced apart flexible catheter tubes disposed within said tubular drive coil, said flexible catheter tubes including an inner flexible catheter tube and an outer flexible catheter tube and having an annular lumen therebetween, said tubes and said annular lumen being sealed at one end and positioned in said drive coil such that a portion of said annular lumen is disposed within said angioplasty balloon, said annular lumen being in fluid communication at the other ends of said tubes with a source of hydraulic fluid, said outer catheter tube having port means disposed therethrough within said balloon and in fluid communication with said portion of said lumen for communicating said hydraulic fluid to the interior of said balloon.

5. An apparatus for treating an obstruction in a vessel according to claim 3, wherein said angioplasty balloon includes a pair of retainer marker rings disposed one at its proximal end and one at its distal end around said drive coil, said proximal and distal ends of said balloon being retained on said drive coil by said rings, said retainer marker rings also assisting in fluoroscopic visualization of said balloon during use of said apparatus for placing said balloon at the proper location with respect to the obstruction.

6. An apparatus for treating an obstruction in a vessel according to claim 3, wherein said tubular drive shaft coil is flexible, and wherein said balloon is longitudinally axially spaced a short distance from said abrasive coil such that said drive shaft coil may flex along its length between said balloon and said abrasive coil.

7. An apparatus for treating an obstruction in a vessel according to claim 2, wherein said means for selectively rotating said coil includes a reversible turbine in engagement with said rotatable drive shaft for selectively rotating said drive shaft in a clockwise or a counterclockwise direction.

8. An apparatus for treating an obstruction in a vessel, comprising:
   a hollow ovaloid tip;
   means for introducing said hollow ovaloid tip inside a vessel proximate to an obstruction;
   said hollow ovaloid tip having an abrasive surface covering at least part of its outer surface;
   means for selectively rotating said hollow ovaloid tip;
   an angioplasty balloon disposed proximal to said hollow ovaloid tip; and
   means for selectively inflating said balloon.

9. A method for treating an obstruction in a vessel, comprising the steps of:
   introducing an instrument comprising a variable diameter coil disposed on its distal end, the coil having an abrasive surface covering at least part of its outer surface, and an angioplasty balloon disposed proximal to said coil, into the vessel proximate to the obstruction in a reduced coil diameter state;
   increasing the diameter of the coil;
   rotating the increased diameter coil at high speed to abrade away the obstruction;
   subsequent to such high speed rotation, reducing the diameter of the coil;
   selectively inflating the angioplasty balloon; and
   withdrawing the instrument from the vessel.

10. A method for treating an obstruction in a vessel, comprising the steps of:
    providing an instrument comprising an ovaloid tip disposed on its distal end, the tip having an abrasive surface covering at least part of its outer surface, and an angioplasty balloon disposed proximal to said tip; introducing said instrument into the vessel proximate to the obstruction;
    selectively rotating the tip at high speed to abrade away the obstruction;
    selectively inflating the angioplasty balloon in the absence of high speed rotation of the tip to cause the enlargement of the vessel or to repair a dissection of vascular tissue at the obstruction site;
    terminating the high speed rotation of the tip;
    deflating the angioplasty balloon; and
    withdrawing the instrument from the vessel.

11. An apparatus for removing an obstruction from a vessel, comprising:
    a coil;
    the circumference of said coil being capable of enlargement by unwinding and compressing the coil;
    means for selectively unwinding and compressing said coil for effecting such enlargement of the circumference of said coil;
    means for introducing said coil in the vessel proximate to the obstruction;
    said coil having an abrasive surface covering at least part of its outer surface;
    means for selectively rotating said coil;
    an angioplasty balloon disposed proximal to said coil; and
    means for selectively inflating said balloon.

* * * * *